United States Patent [19]

Karanewsky

[11] Patent Number: 4,711,884

[45] Date of Patent: Dec. 8, 1987

[54] THIAZINE AND THIAZEPINE CONTAINING COMPOUNDS

[75] Inventor: Donald S. Karanewsky, East Windsor, N.J.

[73] Assignee: E. R. Squibb & Sons, Inc., Princeton, N.J.

[21] Appl. No.: 565,498

[22] Filed: Dec. 27, 1983

Related U.S. Application Data

[63] Continuation-in-part of Ser. No. 470,882, Feb. 28, 1983, Pat. No. 4,460,579.

[51] Int. Cl.[4] ............... C07D 279/06; C07D 281/02; A61K 31/54; A61K 31/55
[52] U.S. Cl. ........................... 514/226; 544/53; 544/54; 544/4; 540/552; 540/544
[58] Field of Search ............... 260/239.3 B, 239.3 R; 544/54, 4; 424/246, 275, 248.52; 514/241, 226

[56] References Cited

U.S. PATENT DOCUMENTS

| | | | |
|---|---|---|---|
| 4,237,129 | 12/1980 | Ondetti | 544/54 |
| 4,374,829 | 2/1983 | Harris et al. | 424/177 |
| 4,438,031 | 3/1984 | Winkley et al. | 544/54 |
| 4,474,778 | 2/1984 | Gordon et al. | 260/239.3 R |
| 4,477,464 | 10/1984 | Slade et al. | 260/239.3 B |

FOREIGN PATENT DOCUMENTS

| | | | |
|---|---|---|---|
| 0046291 | 2/1982 | European Pat. Off. | 260/239.3 R |
| 68173 | 1/1983 | European Pat. Off. | 540/552 |
| 0169475 | 10/1982 | Japan | 260/239.3 B |

Primary Examiner—Glennon H. Hollrah
Assistant Examiner—D. L. Dinner
Attorney, Agent, or Firm—Lawrence S. Levinson; Stephen B. Davis

[57] ABSTRACT

This invention is directed to compounds of the formula

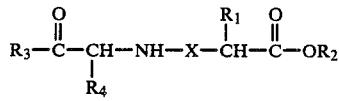

wherein X is a thiazine or thiazepine of the formula

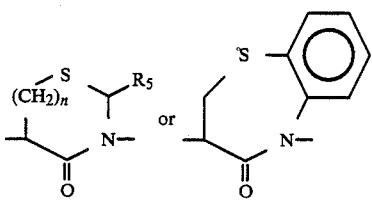

These compounds possess angiotensin converting enzyme inhibition activity and are thus useful as hypotensive agents.

6 Claims, No Drawings

THIAZINE AND THIAZEPINE CONTAINING COMPOUNDS

This application is a continuation-in-part of U.S. Ser. No. 470,882 filed Feb. 28, 1983, now U.S. Pat. No. 4,460,579.

BACKGROUND OF THE INVENTION

Patchett et al. in European Patent Application 68,173 disclose that perhydro-1,4-thiazepin-5-one and perhydro-1,4-thiazocin-5-one derivatives possess angiotensin converting enzyme inhibition activity.

Harris et al. in U.S. Pat. No. 4,374,829 disclose carboxyalkyl dipeptides and derivatives thereof which possess angiotensin converting enzyme inhibition activity.

SUMMARY OF THE INVENTION

This invention is directed to the thiazine and thiazepine compounds of formula I and salts thereof

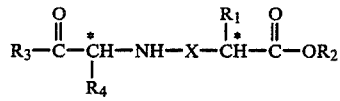

(I)

$R_1$ is hydrogen, lower alkyl, amino substituted lower alkyl, hydroxy substituted lower alkyl, X is

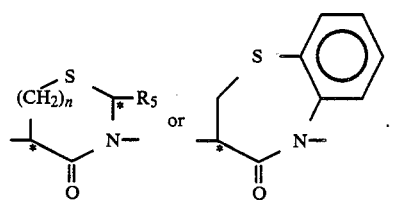

n is one or two.

$R_5$ is hydrogen, lower alkyl, —(CH$_2$)$_m$—cycloalkyl, or

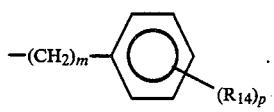

$R_3$ is hydroxy, lower alkoxy, di(lower alkyl)-amino-lower alkoxy, lower alkyl-carbonylamino-lower alkoxy, lower alkyl-carbonyloxy-lower alkoxy,

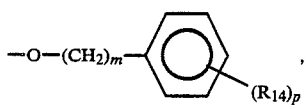

amino, lower alkyl-amino, di (lower alkyl) amino, hydroxyamino, benzylamino, phenethylamino or -O-salt forming ion.

$R_4$ is hydrogen, lower alkyl,

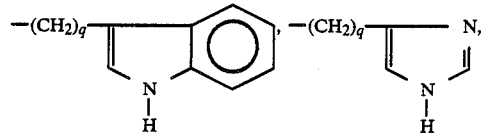

halo substituted lower alkyl, hydroxy substituted lower alkyl,  —(CH$_2$)$_q$—cycloalkyl,  —(CH$_2$)$_q$—carboxy, —(CH$_2$)$_q$—S—lower alkyl,

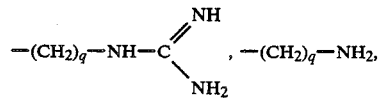

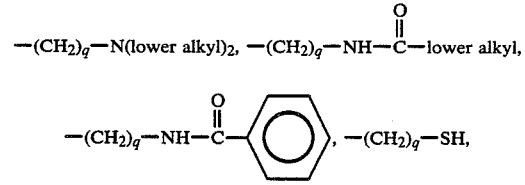

—(CH$_2$)$_q$—N(lower alkyl)$_2$, —(CH$_2$)$_q$—NH—C(=O)—lower alkyl,

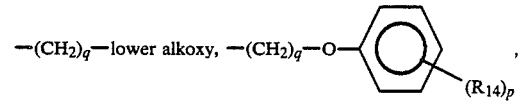

—(CH$_2$)$_q$—lower alkoxy, —(CH$_2$)$_q$—O—

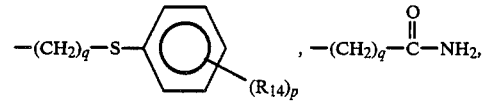

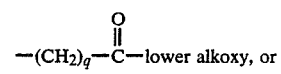

—(CH$_2$)$_q$—C(=O)—lower alkoxy, or

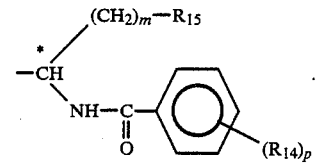

m is zero or an integer from 1 to 4.

q is an integer from 1 to 4.

$R_{14}$ is hydrogen, lower alkyl of 1 to 4 carbons, lower alkoxy of 1 to 4 carbons, lower alkylthio of 1 to 4 carbons, halo, trifluromethyl, or hydroxy.

p is an integer from 1 to 3 provided that p is more than one only if $R_{14}$ is hydrogen, methyl, methoxy, chloro, or fluoro.

$R_{15}$ is lower alkyl, cycloalkyl, or

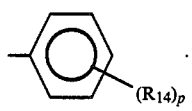

$R_2$ is hydrogen, lower alkyl, benzyl, benzhydryl, trimethylsilylethyl, salt forming ion, or

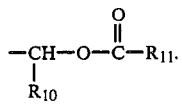

$R_{10}$ is hydrogen, lower alkyl, cycloalkyl, or phenyl.
$R_{11}$ is hydrogen, lower alkyl, lower alkoxy, cycloalkyl, phenyl, benzyl, or phenethyl.

DETAILED DESCRIPTION OF THE INVENTION

This invention in its broadest aspects relates to the thiazine and thiazepine compounds of formula I above, to compositions containing such compounds and to the method of using such compounds as anti-hypertensive agents. The term lower alkyl used in defining various symbols refers to straight or branched chain radicals having up to seven carbons. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo, and fluoro.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, chloromethyl, bromomethyl, etc. Similarly, the terms amino substituted lower alkyl and hydroxy substituted lower alkyl refer to such lower alkyl groups described above in which one or more hydrogens have been replaced by -NH$_2$ or OH, i.e., aminomethyl, 2-aminoethyl, 3-hydroxypropyl, etc.

The compounds of formula I can be prepared as follows. A keto compound of the formula

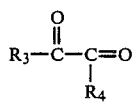 (II)

is reacted with the thiazine or thiazepine ester of the formula

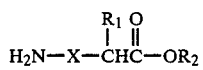 (III)

in the presence of sodium cyanoborohydride to yield the ester of formula I. Preferably, the trimethylsilylethyl ester of the thiazine or thiazepine of formula III is employed in this reaction. The resulting diester product can then be treated to remove the $R_2$ trimethylsilylethyl ester group such as by use of trifluoroacetic acid and anisole or by use of tetrabutylammonium fluoride while leaving the $R_3$ ester group in place. If desired, this monoester product can then be treated with base such as sodium hydroxide to remove the $R_3$ ester group and yield the corresponding diacid compound.

The ester products of formula I wherein

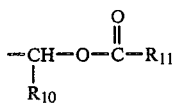

may be obtained by employing the thiazine or thiazepine of formula III in the above reaction with the ester group already in place.

The ester products of formula I wherein $R_2$ is

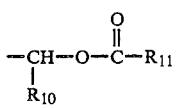

can also be obtained by treating the product of formula I wherein $R_2$ is hydrogen with a molar equivalent of the compound of the formula

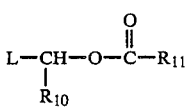 (IV)

wherein L is a leaving group such as chlorine, bromine, tolylsulfonyloxy, etc.

The thiazine or thiazepine ester of formula III wherein $R_5$ is other than hydrogen can be prepared as follows. A phthaloyl amino acid of the formula

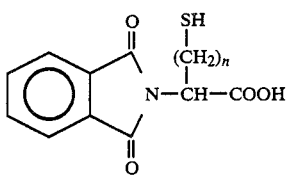 (V)

is reacted with an N-substituted glycine ester of the formula $R_5$—CH=N—CH$_2$—COOR$_2$  VI in the presence of a coupling agent such as dichyclohexylcarbodiimide to yield the N-protected thiazine or thiazepine of the formula

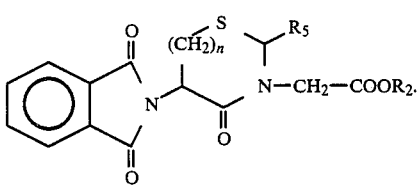 (VII)

Treatment of the compound of formula VII with methylhydrazine removes the phthalimido protecting group and yields the desired thiazine or thiazepine ester of formula III.

The N-protected thiazine or thiazepine of formula VII can also be prepared by cyclizing a sulfoxide of the formula

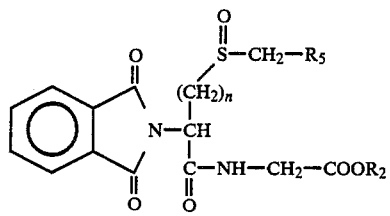

[prepared as set forth by Wolfe et al., Can. J. Chem., Vol. 57, p. 2412–2425 (1979)] by treatment with a mixture of trifluoroacetic acid anhydride and acetic anhydride followed by 2,6-lutidine.

The thiazine or thiazepine ester of formula III wherein $R_5$ is hydrogen can be prepared as follows. A dithiobis amino acid of the formula

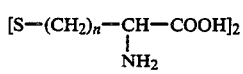

is reacted with N-carboethoxyphthalimide to give the compound of the formula

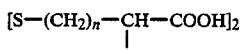
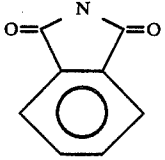

which is treated with a glycine ester hydrochloride in the presence of base and a coupling agent such as carbonyldiimidazole to yield the compound of the formula

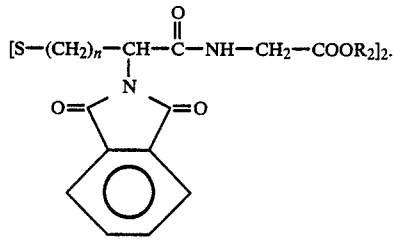

The dithiobis compound of formula XI is treated with zinc dust to yield

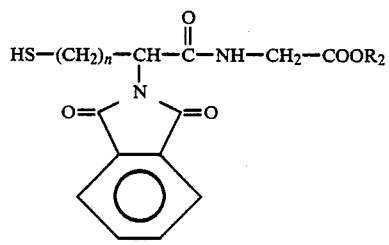

which is then treated with bromomethyl methyl ether in the presence of pyridine to give

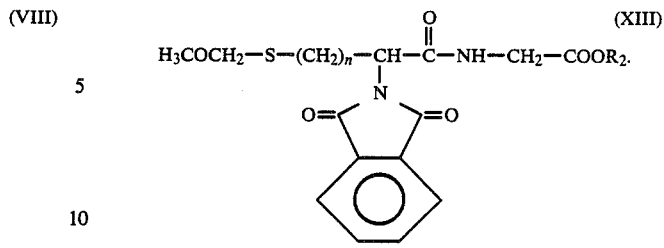

The compound of formula XIII is cyclized by treatment with camphorsulfonic acid to give the N-protected thiazine or thiazepine of the formula

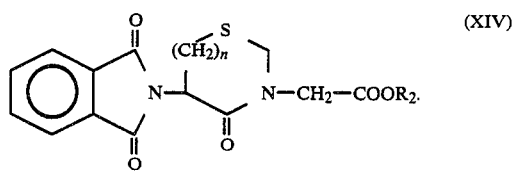

Treatment of the compound of formula XIV with methylhydrazine removes the phthalimido protecting group and yields the desired thiazine or thiazepine ester of formula III.

The thiazepine ester of formula III wherein X is

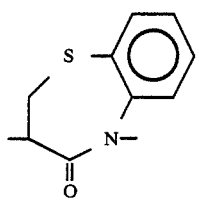

can be prepared as follows. An N-protected serine, for example, a t-butyloxycarbonyl N-protected serine, is treated with methyl iodide and cesium carbonate to yield the corresponding N-protected serine methyl ester. This methyl ester is then treated with diisopropylcarbodiimide and cuprous chloride to yield the N-protected dehydroalanine methyl ester of the formula

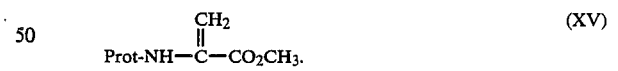

The N-protected dehydroalanine methyl ester of formula XV is reacted with 2-aminothiophenol and 2,6-lutidine to give the compound of formula

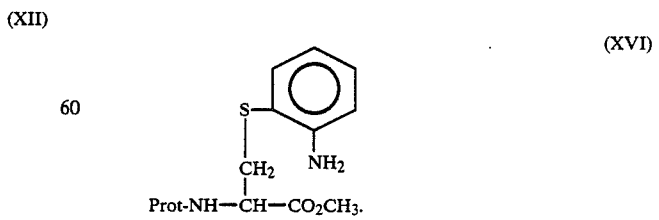

The methyl ester of formula XVI is converted to the carboxylic acid and then cyclized by refluxing in xylene to give the compound of formula

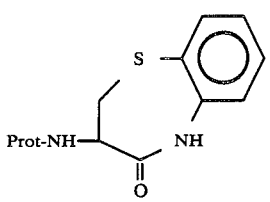

(XVII)

The thiazepine of formula XVII is treated with a bromoacetate of the formula

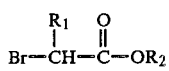

(XVIII)

to yield the compound

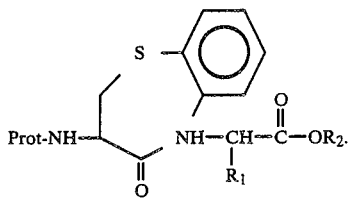

(XIX)

Removal of the protecting group, for example, by treating with hydrogen chloride in ethyl acetate when Prot is t-butyloxycarbonyl yields the desired thiazepine ester of formula III.

In the above reactions if $R_4$ is

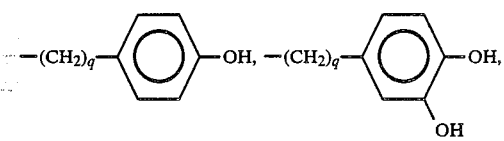

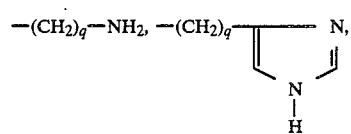

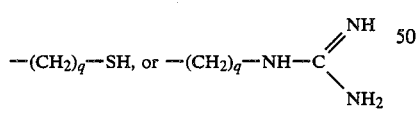

or if $R_1$ is amino or hydroxy substituted lower alkyl then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Preferred compounds of this invention are those of formula I wherein:

$R_3$ is hydroxy, lower alkoxy of 1 to 4 carbons, or —O—alkali metal salt.

$R_4$ is 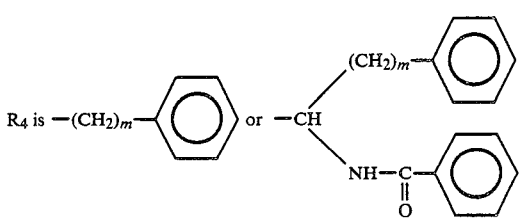

wherein m is zero, one, two or three.

$R_1$ is hydrogen, lower alkyl of 1 to 4 carbons, or —$(CH_2)_4$—$NH_2$.

$R_5$ is hydrogen, lower alkyl of 1 to 4 carbons, or

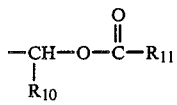

wherein m is zero, one, two or three and $R_{14}$ is hydrogen, methyl, methoxy, methylthio, chloro, bromo, fluoro, or hydroxy.

$R_2$ is hydrogen, lower alkyl of 1 to 4 carbons, alkali metal salt, or

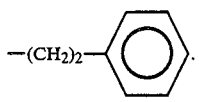

wherein $R_{10}$ is hydrogen, straight or branched chain lower alkyl of 1 to 4 carbons, or cyclohexyl and $R_{11}$ is straight or branched chain lower alkyl of 1 to 4 carbons, cyclohexyl or phenyl.

Most preferred compounds of this invention are those of formula I wherein:

X is

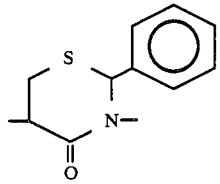

$R_3$ is hydroxy, ethoxy, or —O—alkali metal salt.
$R_4$ is

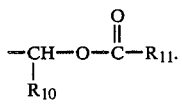

$R_1$ is hydrogen.
$R_2$ is hydrogen, alkali metal salt, or

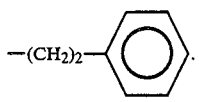

$R_{10}$ is hydrogen, straight or branched chain lower alkyl of 1 to 4 carbons, or cyclohexyl.

$R_{11}$ is straight or branched chain lower alkyl of 1 to 4 carbons.

The compounds of this invention wherein $R_2$ is hydrogen or $R_3$ is hydroxy form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The symbol * is used to represent various asymmetric centers which may be present in the compounds of formula I. Thus, the compounds of this invention can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrene-divinylbenzene polymer resin.

EXAMPLE 1

(5R)-5-[(1-Carboxy-3-phenylpropyl)amino]dihydro4-oxo-2-phenyl-2H-1,3-thiazine-3(4H)-acetic acid (B-slow isomer)

(a) N-Phthaloyl-L-cysteine

A solution of N,N'-diphthaloyl-L-cystine (19.5 g., 38.9 mmole) in a mixture of trifluoroacetic acid (60 ml.) and dry tetrahydrofuran (200 ml.) is cooled in an ice-bath under nitrogen and treated with zinc dust (15.3 g., 233.4 mmole) in three equal portions over a period of 15 minutes. The reaction is stirred cold for 2 hours, then filtered (celite) and concentrated in vacuo. The residue is partitioned between 600 ml. of ethyl acetate:ether (5:1) and a water-brine mixture. The organic layer is washed with water, brine and dried (MgSO$_4$). Removal of the solvents in vacuo yields 21.9 g. of crude product which is flash chromatographed on silica gel (400 g.) eluting with toluene:acetic acid (6:1). Fractions containing the desired product are combined to give 12.1 g. of N-phthaloyl-L-cysteine as an oil. $[\alpha]_D = -54.2°$ (c=1, methanol). TLC (toluene/acetic acid; 6:1) spot at $R_f = 0.30$.

(b) N-Benzylidineglycine, ethyl ester

A mixture of glycine, ethyl ester, hydrochloride (10 g., 71.6 mmole), triethylamine (14.5 g., 143.2 mmole) and anhydrous MgSO$_4$ (6.0 g., 50.1 mmole) in dry methylene chloride (150 ml.) is treated with a solution of benzaldehyde (7.6 g., 71.6 mmole) in methylene chloride (10 ml.) added over a period of 15 minutes. After 5 hours, the reaction mixture is filtered, concentrated in vacuo, and then partitioned between 400 ml. of ether and 50 ml. of water. The organic layer is washed with water and brine, dried (MgSO$_4$), and concentrated in vacuo to give 12.1 g. of N-benzylidineglycine, ethyl ester.

(c) (5R)-Dihydro-5-phthalimido-4-oxo-2-phenyl-2H1,3-thiazine-3(4H)-acetic acid, ethyl ester (isomers A and B)

To a solution of N-phthaloyl-L-cysteine (15.8 g., 62.8 mmole) and N-benzylidineglycine, ethyl ester (12.3 g., 64.3 mmole) in dry chloroform (160 ml.) cooled in an ice bath under nitrogen is added dicyclohexylcarbodiimide (13.0 g., 62.8 mmole) in one portion. After 2 hours, the cold reaction mixture is filtered, concentrated in vacuo and redissolved in a mixture of ether (500 ml.) and chloroform (200 ml.). The organic extract is washed with saturated aqueous sodium bicarbonate, water, 5% potassium bisulfate and brine, dried (MgSO$_4$) and concentrated in vacuo to give 23.8 g. of crude product. Flash chromatography on silica (600 g.) eluting with hexane: ethyl acetate (3:1) yields 15.6 g. of (5R)-dihydro-5-phthalimido-4-oxo-2-phenyl-2H-1,3-thiazine-3(4H)-acetic acid, ethyl ester as a diastereomeric mixture.

This mixture is refluxed in 500 ml. of ether for 4 hours, then cooled in an ice-bath and filtered to yield 5.9 g. of (5R)-dihydro-5-phthalimido-4-oxo-2-phenyl-2H-1,3-thiazine-3(4H)-acetic acid, ethyl ester (isomer A); m.p. 166°–168°; [α]$_D$= −72.9° (c=1, chloroform). TLC (hexane/ethyl acetate; 1:1)spot at R$_f$=0.40.

Anal. calc'd. for C$_{22}$H$_{20}$N$_2$O$_5$S: C, 62.25; H, 4.75; N, 6.60; S, 7.55. Found: C, 62.21; H, 4.82; N, 6.63; S, 7.52.

Trituration of the remainder of the diastereomeric product mixture with 125 ml. of refluxing ether affords a second batch of isomer A (0.9 g., m.p. 162°–164°). The residue is triturated with ether to give 0.75 g. of insoluble substance (presumably largely isomer A) and 7.1 g. of material enriched in isomer B. The enriched isomer B (6.0 g.) is chromatographed on two connected Waters Prep LC columns eluted with hexane:ethyl acetate (3:1). Pooling of the product containing fractions yields 4.8 g. of purified (5R)-dihydro-5-phthalimido-4-oxo-2-phenyl-2H-1,3-thiazine-3(4H)-acetic acid, ethyl ester (isomer B);m.p. 66°–68°; [α]$_D$=101.2° (c=1, chloroform). TLC same as isomer A.

Anal. calc'd. for C$_{22}$H$_{20}$N$_2$O$_5$S.0.2 H$_2$O: C, 61.83; H, 4.79; N, 6.55; S, 7.50. Found: C, 61.83; H, 5.07; N, 6.25; S, 7.42.

(d)
(5R)-Dihydro-5-Phthalimido-4-oxo-2-phenyl-2H-1,3-thiazine-3(4H)-acetic acid, 2-(trimethylsilyl)ethyl ester (isomer B)

A mixture of (5R)-dihydro-5-phthalimido-4-oxo-2-phenyl-2H-1,3-thiazine-3(4H)-acetic acid, ethyl ester (isomer B) (2.5 g., 5.9 mmole), 2-trimethylsilylethanol (14.0 g., 118 mmole), and titanium (IV) ethoxide (338 mg., 1.48 mmole) is heated at 100° under nitrogen for 5 hours and then cooled to room temperature. The reaction mixture is then diluted with 200 ml. of ether and stirred with 25 ml. of 1N hydrochloric acid for 10 minutes. Next, the organic solution is separated, rinsed with water, saturated sodium bicarbonate, water, and brine, dried (MgSO$_4$), and concentrated in vacuo. Most of the excess 2-trimethylsilylethanol is removed by distillation using a 40° oil bath and an ice-cooled receiving flask. After further pumping in vacuo, the residue (3.2 g.) is flash chromatographed on 160 g. of LPS-1 silica gel eluted with hexane:ethyl acetate (5:1) to give 2.2 g. of (5R)-dihydro-5-phthalimido-4-oxo-2-phenyl-2H-1,3-thiazine-3(4H)-acetic acid, 2-(trimethylsilyl)ethyl ester (isomer B); m.p. 65°–66°; [α]$_D$= −75.0° (C=1, chloroform). TLC (hexane: ethyl acetate; 2:1) spot at R$_f$=0.46.

Anal. calc'd. for C$_{25}$H$_{28}$N$_2$O$_5$SSi: C, 60.46; H, 5.68; N, 5.64; S, 6.46. Found: C, 60.44; H, 5.69; N, 5.50; S, 6.43.

(e) (5R)-Dihydro-5-amino-4-oxo-2-phenyl-2H-1,3-thiazine-3(4H)-acetic acid, 2-(trimethylsilyl)-ethyl ester (isomer B)

A solution of (5R)-dihydro-5-phthalimido-4-oxo-2-phenyl-2H-1,3-thiazine-3(4H)-acetic acid, 2-(trimethylsilyl)ethyl ester (isomer B) (2.01 g., 4.05 mmole) in dry chloroform (9 ml.) under nitrogen at room temperature is treated with methylhydrazine (317 mg., 6.88 mmole). After 12 hours, an additional 0.1 ml. of methylhydrazine is added and the reaction is stoppered and stirred overnight. The reaction mixture is then diluted with an additional 100 ml. of ether and the solution is rinsed with 25 ml. portions of saturated sodium bicarbonate, water, and brine, dried (MgSO$_4$), and concentrated in vacuo to give 1.55 g. of crude (5R)-dihydro-5-amino-4-oxo-2-phenyl-2H-1,3-thiazine-3(4H)-acetic acid, 2-(trimethylsilyl)ethyl ester (isomer B); [α]$_D$= −47.3° (c=1, chloroform).

(f)
(5R)-5-[[1-(Ethoxycarbonyl)-3-phenylpropyl]amino]-dihydro-4-oxo-2-phenyl-2H-1,3-thiazine-3(4H)-acetic acid, 2-(trimethylsilyl)ethyl ester (B fast and slow isomers)

To a solution of (5R)-dihydro-5-amino-4-oxo-2-phenyl-2H-1,3-thiazine-3(4H)-acetic acid, 2-(trimethylsilyl)ethyl ester (isomer B) (1.55 g., 4.05 mmole) in 11 ml. of isopropanol is added ethyl-2-oxo-4-phenylbutyrate (4.18 g., 20.2 mmole). The above mixture, at room temperature under nitrogen, is treated with p-toluenesulfonic acid, monohydrate (386 mg., 2.03 mmole) followed by 4.5 g. of freshly pulverized 3A° molecular sieves. This mixture is stirred for 1 hour while keeping the pH between 6 and 8 by adding solid sodium bicarbonate. Next, a solution of sodium cyanoborohydride (509 mg., 8.1 mmole) in isopropanol (8.1 ml.) is added over a period of 5 hours while keeping the pH between 6 and 8 by adding p-toluenesulfonic acid, monohydrate. Upon completion of the addition, the reaction is stirred at room temperature overnight, diluted with 150 ml. of ether, and filtered. The filtrate is rinsed with 30 ml. portions of water, 10% potassium bisulfate, water, saturated sodium bicarbonate, water, and brine, then dried (MgSO$_4$), and concentrated in vacuo to give 5.4 g. of crude product. Removal of most of the by-product, ethyl-2-hydroxy-4-phenylbutyrate, is accomplished by chromatography. The resulting crude mixture of diastereomers (1.6 g.) is flash chromatographed on 100 g. of LPS-1 silica gel eluted with petroleum ether:ether (7:2). This yields 821 mg. of (5R)-5-[[1-(ethoxycarbonyl)-3-phenylpropyl]amino]dihydro-4-oxo-2-phenyl-2H-1,3-thiazine-3(4H)-acetic acid, 2-(trimethylsilyl)ethyl ester (B-slow isomer), [α]$_D$= −29.8° (c=1, chloroform).

Anal. Calc'd. for C$_{29}$H$_{40}$N$_2$O$_5$SSi: C, 62.55; H, 7.24; N, 5.03; S, 5.76. Found: C, 62.25; H, 7.30; N, 4.91; S, 5.56.

The fraction from the above flash column contains 525 mg. of the fast moving diastereomer. This material is further purified by hydrogenation in 40 ml. of ethyl acetate at 50 psi in the presence of 125 mg. of 10% palladium/carbon catalyst. After 20 hours, the solution is filtered, concentrated in vacuo and the residue (450 mg.) is flash chromatographed on 22 g. of LPS-1 silica gel eluting with petroleum ether:ether (3:1). Pooling of the product containing fractions yields 325 mg. of (5R)-5-[[1-(ethoxycarbonyl)-3-phenylpropyl]amino]dihydro-4-oxo-2-phenyl-2H-1,3-thiazine-3(4H)-acetic acid, 2-

(trimethylsilyl)ethyl ester (B-fast isomer), [α]$_D$= −22.4° (c=1, chloroform).

Anal. calc'd. for $C_{29}H_{40}N_2O_5SSi$: C, 62.55; H, 7.24; N, 5.03; S, 5.76. Found: C, 62.73; H, 7.43; N, 4.82; S, 5.47.

(g)

(5R)-5-[[1-(Ethoxycarbonyl)-3-phenylpropyl]amino]-dihydro-4-oxo-2-phenyl-2H-1,3-thiazine-3(4H)-acetic acid (B-slow isomer)

A mixture of trifluoroacetic acid (8 ml.) and anisole (0.4 ml.) is cooled in an ice-water bath under nitrogen and treated with (5R)-5[[1-(ethoxycarbonyl)-3-phenylpropyl]amino]dihydro-4-oxo-2-phenyl-2H-1,3-thiazine-3(4H)-acetic acid, 2-(trimethylsilyl)ethyl ester (B-slow isomer) (400 mg., 0.72 mmole) dissolved in dry methylene chloride (4 ml.). The cooling bath is removed and the reaction is stirred at ambient temperature for 3 hours, then concentrated in vacuo and azeotroped with toluene. The crude product (440 mg.) is chromatographed on 150 ml. of HP-20 eluted with a gradient from 400 ml. of water:acetonitrile (5:4) to 400 ml. of 100% acetonitrile. The product containing fractions are pooled, evaporated, then precipitated from ethanol (10 ml.) by the addition of water (300 ml.). By this method 171 mg. of (5R)-5-[[1-(ethoxycarbonyl)-3-phenylpropyl]amino]dihydro-4-oxo-2-phenyl-2H1,3-thiazine-3(4H)-acetic acid (B-slow isomer) are obtained; m.p. 130°-135°; [α]$_D$= −36.1° (c=1, methanol). TLC (ethyl acetate:pyridine:acetic acid: water; 100:20:6:11) spot at $R_f$=0.79.

Anal. calc'd. for $C_{24}H_{28}N_2O_5S$: C, 63.13; H, 6.18; N, 6.14; S, 7.02. Found: C, 63.20; H, 6.26; N, 6.12; S, 6.97.

(h)

(5R)-5-[(1-Carboxy-3-phenylpropyl)amino]dihydro4-oxo-2-phenyl-2H-1,3-thiazine-3(4H)-acetic acid (B-slow isomer)

A solution of the product from part (g) (50 mg., 0.11 mmole) in methanol (0.2 ml.) is cooled in an ice-water bath under argon and treated with 1N aqueous sodium hydroxide (0.241 ml.). The cooling bath is removed and the reaction is stirred at room temperature for 5 hours. The reaction is then quenched directly onto a 2 ml. AG 50W-X2(H+) column and eluted with water. The elution solvent is then dhanged to 3% aqueous pyridine to elute about 40 mg. of crude product. Final purification is carried out on a 15×180 mm. HP-20 column eluted with a gradient from 200 ml. of acetonitrile:water (1:1) to 200 ml. of 100% acetonitrile. Pooling of the product containing fractions yields 34 mg. of (5R)-5-[(1-carboxy-3phenylpropyl)amino]dihydro-4-oxo-2-phenyl-2H-1,3-thiazine-3(4H)-acetic acid (B-slow isomer) as a monohydrate; m.p. 132°-138°; [α]$_D$=40.8° (c=0.5, 5% aqueous sodium bicarbonate). TLC (isopropanol:N-H$_4$OH: water; 7:2:1) spot at $R_f$=0.63.

Anal. calc'd. for $C_{22}H_{24}N_2O_5S$.1.0 $H_2O$: C, 59.17; H, 5.87; N, 6.28; S, 7.18. Found: C, 59.36; H, 5.53; N, 6.35; S, 7.18.

EXAMPLE 2

(5R)-5-[(1-Carboxy-3-phenylpropyl)amino]dihydro4-oxo-2-phenyl-2H-1,3-thiazine-3(4H)-acetic acid (B-fast isomer)

(a)

(5R)-5-[[1-(Ethoxycarbonyl)-3-phenylpropyl]amino]-dihydro-4-oxo-2-phenyl-2H-1,3-thiazine-3(4H)-acetic acid (B-fast isomer)

A mixture of trifluoroacetic acid (6 ml.) and anisole (0.3 ml.) is cooled in an ice-bath under nitrogen and treated with (5R)-5[[1-(ethoxycarbonyl)-3-phenylpropyl]amino]dihydro-4-oxo-2-phenyl-2H-1,3-thiazine-3(4H)-acetic acid, 2-(trimethylsilyl)ethyl ester (B-fast isomer) (315 mg., 0.57 mmole) dissolved in dry methylene chloride (4 ml.). The cooling bath is removed and-the reaction is stirred at room temperature under nitrogen for 3 hours, then concentrated in vacuo and azeotroped with toluene to yield 363 mg. of crude product. Chromatography on 150 ml. of HP-20 eluted with a gradient from 400 ml. of water:acetonitrile (5:4) to 400 ml. of 100% acetonitrile yields 200 mg. of (5R)-5-[[(1-(ethoxycarbonyl)-3-phenylpropyl]amino]-dihydro-4-oxo-2-phenyl-2H-1,3-thiazine-3(4H)-acetic acid (B-fast isomer); m.p. 160°-165° ; [α]$_D$= −24.4° (c=0.5, methanol).

TLC (ethyl acetate:pyridine:acetic acid:water; 100:20:6:11) spot at $R_f$=0.70 (minor spot at $R_f$=0.80).

Anal. calc'd. for $C_{24}H_{28}N_2O_5S$: C, 63.13; H, 6.18; N, 6.14; S, 7.02. Found: C, 63.39; H, 6.37; N, 5.94; S, 6.92.

(b)

(5R)-5-[(1-Carboxy-3-phenylpropyl)amino]dihydro4-oxo-2-phenyl-2H-1,3-thiazine-3(4H)-acetic acid (B-fast isomer)

A solution of the product from part (a) (50 mg., 0.11 mmole) in methanol (0.2 ml.) is cooled in an ice-water bath under argon and treated with 1 N aqueous sodium hydroxide (0.241 ml.). The cooling bath is removed and the reaction is stirred at room temperature for 7 hours, then quenched directly onto a 2 ml. AG50W-X2(H+) column. The exchange column is initially eluted with several ml. of water then with 3% aqueous pyridine to give 42 mg. of crude product after removal of solvents. The crude product is purified by gradient elution on a 15×180 mm. HP-20 column run from 210 ml. of water::acetonitrile (2:1) to 210 ml. of 100% acetonitrile taking about 3 ml/2 min. fractions. The product containing fractions are pooled with methanol rinses and evaporated to give 31.3 mg. of (5R)-5-[(1-carboxy-3-phenylpropyl)amino]dihydro-4-oxo-2-phenyl-2H-1,3-thiazine-3(4H)-acetic acid(B-fast isomer) as a monohydrate; m.p. 131°-134°; [α]$_D$= −40.4° (c=0.5, 5% aqueous sodium bicarbonate). TLC (isopropanol:NH$_3$:water; 7:2:1) spot at $R_f$=0.51.

Anal.calc'd. for $C_{22}H_{24}N_2O_5S$ .1.0 $H_2O$: C, 59.17; H, 5.87; N, 6.28; S, 7.18. Found: C, 59.24; H, 5.58; N, 6.32; S, 7.00.

EXAMPLE 3

(5R)-5-[(1-Carboxy-3-phenylpropyl)amino]dihydro-4-oxo-2-phenyl-2H-1,3-thiazine-3(4H)-acetic acid (A-slow isomer)

(a)

(5R)-Dihydro-5-phthalimido-4-oxo-2-phenyl-2H-1,3-thiazine-3(4H)-acetic acid, 2-(trimethylsilyl)ethyl ester (isomer A)

A mixture of (5R)-dihydro-5-phthalimido-4-oxo-2-phenyl-2H-1,3-thiazine-3(4H)-acetic acid, ethyl ester (isomer A), from Example 1(c), (2.8 g., 6.6 mmole), 2-trimethylsilylethanol (15.37 g., 130 mmole), and titanium (IV) ethoxide (376 mg., 1.65 mmole) is heated at 100° under nitrogen for 5.5 hours, then cooled to room temperature overnight. The reaction mixture is diluted with ether (200 ml.), and stirred with 1N hydrochloric acid (25 ml.) for 10 minutes. The organic layer is separated, rinsed with saturated aqueous sodium bicarbonate, water, and brine, dried (MgSO$_4$), and concentrated in vacuo. Most of the excess 2-trimethylsilylethanol is removed by distillation using a 40° oil bath and an ice-cooled receiving flask. After continued pumping overnight in vacuo, the residue(4.3 g.) is flash chromatographed on 215 g. of LPS-1 silica gel eluted with hexane:ethyl acetate (5:1) to yield 2.7 g. of (5R)-dihydro-5-phthalimido-4-oxo-2-phenyl-2H-1,3-thiazine-3(4H)-acetic acid, 2-(trimethylsilyl)ethyl ester (isomer A); m.p. 58°–60°; $[\alpha]_D = -53.6°$ (c=1, chloroform). TLC (hexane:ethyl acetate; 2:1) spot at $R_f=0.32$.

Anal. calc'd. for $C_{25}H_{28}N_2O_5SSi$ C, 60.46; H, 5.68; N, 5.64; S, 6.46. Found: C, 60.20; H, 5.71; N, 5.56; S, 6.42.

(b)

(5R)-Dihydro-5-amino-4-oxo-2-phenyl-2H-1,3-thiazine-3(4H)-acetic acid, 2-(trimethylsilyl)ethyl ester (isomer A)

A solution of (5R)-dihydro-5-phthalimido-4-oxo-2-phenyl-2H-1,3-thiazine-3(4H)-acetic acid, 2-(trimethylsilyl)ethyl ester(isomer A) (2.7 g., 5.43 mmole) in dry chloroform (12 ml.) under nitrogen at room temperature is treated with 425 mg. of methylhydrazine (9.24 mmole) and the reaction is stoppered. After 48 hours, an additional 0.15 ml. of methylhydrazine is added, and the reaction is stoppered and stirred overnight. The reaction mixture is then diluted with 70 ml. of ether, stirred for 10 minutes, and filtered. The filtrate is diluted with ether (150 ml.), washed with 35 ml. portions of aqueous sodium bicarbonate, water, and brine, dried (MgSO$_4$), and concentrated in vacuo to give 2.1 g. of (5R)-dihydro-5-amino-4-oxo-2-phenyl-2H-1,3-thiazine-3(4H)-acetic acid, 2-(trimethylsilyl)ethyl ester (isomer A); $[\alpha]_D = +35.2°$ (c=1, chloroform).

(c)

(5R)-5-[[1-(Ethoxycarbonyl)-3-phenylpropyl]amino]-dihydro-4-oxo-2-phenyl-2H-1,3-thiazine-3(4H)-acetic acid, 2-(trimethylsilyl)ethyl ester (A-fast and slow isomers)

To a solution of (5R)-dihydro-5-amino-4-oxo-2-phenyl-2H-1,3-thiazine-3(4H)-acetic acid, 2-(trimethylsilyl)ethyl ester (isomer A) (2.1 g., 5.43 mmole) in isopropanol (15 ml.) under nitrogen at room temperature is added ethyl-2-oxo-4-phenylbutyrate (5.6 g., 27.15 mmole) followed by p-toluenesulfonic acid, monohydrate (518 mg., 2.72 mmole) and finally freshly pulverized 3A° molecular sieves (6.0 g.). The mixture is stirred for one hour while the pH is kept between 6 and 8 by adding solid sodium bicarbonate. A solution of sodium cyanoborohydride (682 mg., 10.86 mmole) in isopropanol (10.9 ml.) is added to the reaction over a 5 hour period while keeping the pH between 6 and 8 by adding p-toluenesulfonic acid, monohydrate. After the addition is completed, the reaction is stirred at room temperature overnight, then diluted with ether (200 ml.), and filtered. The filtrate is rinsed with 40 ml. portions of 10% potassium bisulfate, water, saturated sodium bicarbonate, water, and brine, dried (MgSO$_4$), and concentrated in vacuo to yield 8.6 g. of crude product. Further purification is accomplished chromatographically using 350 g. of Activity II neutral alumina eluted with ether:acetonitrile (20:1). The resulting crude product obtained (800 mg.) is hydrogenated by dissolving in ethyl acetate (70 ml.), adding 200 mg. of 10% palladium/carbon catalyst and shaking on a Parr apparatus at an initial hydrogen pressure of 50 psi overnight. The resulting crude mixture of diastereomers (760 mg.) is flash chromatographed on 50 g. of LPS-1 silica gel eluting with petroleum ether:ether (3:1).

This column yields 240 mg. of (5R)-5-[[1-(ethoxycarbonyl)-3-phenylpropyl]amino]dihydro-4-oxo-2-phenyl-2H-1,3-thiazine-3(4H)-acetic acid, 2-(trimethylsilyl)ethyl ester (A-fast isomer); $[\alpha]_D = +26.1°$ (c=1, chloroform). TLC (petroleum ether:ether; 3:1) spot at $R_f=0.10$.

Anal. Calc'd. for $C_{29}H_{40}N_2O_5SSi$ C, 62.55; H, 7.24; N, 5.03; S, 5.76. Found: C, 62.31; H, 7.50; N, 4.94; S, 5.74.

The column also yields 400 mg. of (5R)-5-[[1-(ethoxycarbonyl)-3-phenylpropyl]amino]dihydro-4-oxo-2-phenyl-2H-1,3-thiazine-3(4H)-acetic acid, 2-(trimethylsilyl)ethyl ester (A-slow isomer); $[\alpha]_D = +14.5°$ (c=1, chloroform). TLC (petroleum ether:ether; 3:1) spot at $R_f=0.06$.

Anal. Calc'd. for $C_{29}H_{40}N_2O_5SSi$ C, 62.55; H, 7.24; N, 5.03; S, 5.76. Found: C, 62.46; H, 7.32; N, 4.94; S, 5.64.

(d)

(5R)-5-[[1-(Ethoxycarbonyl)-3-phenylpropyl]amino]-dihydro-4-oxo-2-phenyl-2H-1,3-thiazine-3(4H)-acetic acid (A-slow isomer)

A solution of trifluoroacetic acid (8 ml.) and anisole (0.4 ml.) is cooled in an ice-water bath under nitrogen and treated with (5R)-5-[[1-(ethoxycarbonyl)-3-phenylpropyl]amino]dihydro4-oxo-2-phenyl-2H-1,3-thiazine-3(4H)-acetic acid, 2-(trimethylsilyl)ethyl ester (A-slow isomer) (400 mg., 0.72 mmole) dissolved in dry methylene chloride (4 ml.). The cooling bath is removed, and the reaction is stirred at room temperature for 3 hours, concentrated in vacuo and azeotroped with toluene. The crude product (398 mg.) is chromatographed on 150 ml. of HP-20 eluted with a gradient from 400 ml. of water:acetonitrile (5:4) to 400 ml. of 100% acetonitrile. The product containing fractions are pooled and concentrated in vacuo to give 275 mg. of (5R)-5-[[1-(ethoxycarbonyl)-3-phenylpropyl]amino]dihydro-4-oxo-2-phenyl-2H-1,3-thiazine-3(4H)-acetic acid (A-slow isomer); m.p. 47°–52°; $[\alpha]_D = +21.4°$ (c=0.5, methanol). TLC (ethyl acetate:pyridine:acetic acid:water; 100:20:6:11) spot at $R_f=0.83$.

Anal. Calc'd. for $C_{24}H_{28}N_2O_5S \cdot 0.8 H_2O$: C, 61.20; H, 6.34; N, 5.95; S, 6.81. Found: C, 61.20; H, 6.07; N, 5.94; S, 6.68.

(e) (5R)-5-[(1 Carboxy-3-phenyloropyl)amino]dihydro-4-oxo-2-phenyl-2H-1,3-thiazine-3(4H)-acetic acid (A-slow isomer)

A solution of the product from part(d) (50 mg., 0.11 mmole) in methanol (0.2 ml.) is cooled in an ice-water bath under nitrogen and treated with 1N sodium hydroxide (0.24 ml.). The ice bath is removed, and the reaction is stirred at ambient temperature for 5 hours. The reaction is then quenched directly onto a 2 ml. AG50W-X2(H+) column and washed with water. The desired product is eluted with 3% aqueous pyridine to give 46 mg. of crude product. Final purification is carried out on a 50 ml. HP-20 column eluted with a gradient from 200 ml. of water:acetonitrile (2:1) to 200 ml. of 100% acetonitrile. The product containing fractions are concentrated in vacuo, triturated with cold water, and filtered to give 24 mg. of (5R)-5-[(1-carboxy-3-phenylpropyl)amino]dihydro-4-oxo-2-phenyl-2H-1,3-thiazine-3(4H)-acetic acid (A-slow isomer) as a monohydrate; m.p. 190°-192°; $[\alpha]_D = +55.4°$ (c=0.5, 5% aqueous sodium bicarbonate). TLC (isopropanol: NH$_4$OH:water; 7:2:1)spot at R$_f$=0.56.

Anal. Calc'd. for $C_{22}H_{24}N_2O_5S$. 1.0 H$_2$O: C, 59.07; H, 5.86; N, 6.26; S, 7.16. Found: C, 59.07; H, 5.58; N, 6.10; S, 7.05.

EXAMPLE 4

(5R)-5-[(1-Carboxy-3-phenylpropyl)amino]dihydro-4-oxo-2-phenyl-2H-1,3-thiazine-3(4H)-acetic acid (A-fast isomer)

(a)

(5R)-5-[[1-(Ethoxycarbonyl)-3-phenylpropyl]amino]-dihydro-4-oxo-2-phenyl-2H-1,3-thiazine3(4H)-acetic acid (A-fast isomer)

A solution of trifluoroacetic acid (4 ml.) and anisole (0.3 ml.) is cooled in an ice-water bath under nitrogen and treated with a solution of (5R)-5-[[1-(ethoxycarbonyl)-3-phenylpropyl]amino]dihydro-4-oxo-2-phenyl-2H-1,3-thiazine3(4H)-acetic acid, 2-(trimethylsilyl)ethyl ester (A-fast isomer), from Example 3(c), (223 mg., 0.4 mmole) in dry methylene chloride (2 ml.). The cooling bath is removed and the reaction mixture is stirred at ambient temperature under nitrogen for 3 hours, concentrated in vacuo, and azeotroped with toluene to give 240 mg. of crude product. Chromatography on 150 ml. of HP-20 eluting with a gradient from 400 ml. water:acetonitrile (5:4) to 400 ml. of 100% acetonitrile yields 169 mg. of (5R)-5-[[1-(ethoxycarbonyl)-3-phenyl-propyl]amino]dihydro-4-oxo-2-phenyl-2H-1,3-thiazine-3(4H)-acetic acid (A fast isomer); m.p. 45°-52°; $[\alpha]_D = +25.2°$ (c=0.5, methanol). TLC (ethyl acetate:pyridine:acetic acid:water; 100:20:6:11) spot at R$_f$=0.56.

Anal. Calc'd. for $C_{24}H_{28}N_2O_5S$. 0.3 H$_2$O: C, 62.39; H, 6.24; N, 6.06; S, 6.94. Found: C, 62.61; H, 6.07; N, 5.61; S, 6.91.

(b)

(5R)-5-[(1-Carboxy-3-phenylpropyl)amino]dihydro-4-oxo-2-phenyl-2H-1,3-thiazine-3(4H)-acetic acid (A-fast isomer)

A solution of the product from part (a) (49 mg., 0.11 mole) in methanol (0.2 ml.) is cooled in an ice-water bath under nitrogen and treated with 1N sodium hydroxide (0.24 ml., 0.241 mmole). The cooling bath is removed, the reaction is stirred for 6 hours at room temperature, and then quenched directly onto 2 ml. AG50W-X2(H+) column. The column is initially washed with a few volumes of water, then the product is eluted with 3% aqueous pyridine to give 35 mg. of (5R)-5-[(1-carboxy-3-phenylpropyl)amino]dihydro-4-oxo-2-phenyl-2H-1,3-thiazine-3(4H)-acetic acid (A-fast isomer) as a 1.2 hydrate; m.p. 146°-150°; $[\alpha]_D = +52.8°$ (c=0.5, 5% aqueous sodium bicarbonate). TLC (isopropanol:NH$_4$OH: water; 7:2:1) spot at R$_f$=0.52.

Anal. Calc'd. for $C_{22}H_{24}N_2O_5S$ . 1.2 H$_2$O: C, 58.70; H, 5.91; N, 6.22; S, 7.12. Found: C, 58.70; H, 5.70; N, 6.22; S, 7.16.

EXAMPLES 5-31

Following the procedure of Examples 1 to 4 but employing the keto compound shown in Col. I and the thiazine ester shown in Col. II, one obtains the product shown in Col. III. The R$_2$ and R$_3$ ester groups can be removed to give the corresponding diacid which can then be converted to a salt. In the case of Examples 28 to 31, only the R$_3$ ester group would be removed. The R$_3$ and R$_4$ protecting groups shown in Examples 16, 18, and 20 to 22 are removed as the last step of the synthesis.

Col. I

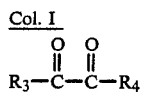

Col. II

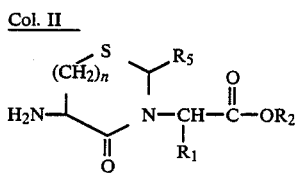

Col. III

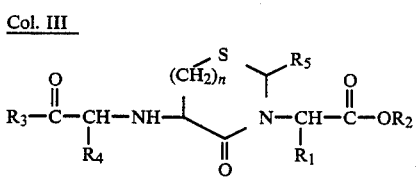

| Example | R$_3$ | R$_4$ | n | R$_5$ | R$_1$ | R$_2$ |
|---|---|---|---|---|---|---|
| 5 | —OC$_2$H$_5$ | —(CH$_2$)$_2$—⟨phenyl⟩ | 2 | —⟨phenyl⟩ | —CH$_3$ | —C$_2$H$_4$Si(CH$_3$)$_3$ |

-continued

| Example | R₃ | R₄ | n | R₅ | R₁ | R₂ |
|---|---|---|---|---|---|---|
| 6 | $-OC_2H_5$ | $-CH_2-C_6H_5$ | 1 | $-H$ | $-H$ | $-C_2H_4Si(CH_3)_3$ |
| 7 | $-OC_2H_5$ | $-CH_2-O-C_6H_5$ | 2 | $-H$ | $-H$ | $-C_2H_4Si(CH_3)_3$ |
| 8 | $-OC_2H_5$ | $-CH_2-C_6H_4-OCH_3$ | 1 | $-CH_3$ | $-H$ | $-C_2H_4Si(CH_3)_3$ |
| 9 | $-OH$ | $-CH_3$ | 2 | $-H$ | $-H$ | $-C_2H_4Si(CH_3)_3$ |
| 10 | $-OCH_2N(CH_3)_2$ | $-CH_2-C_6H_5$ | 1 | $-C_6H_5$ | $-CF_3$ | $-C_2H_4Si(CH_3)_3$ |
| 11 | $-OCH_2NHC(O)CH_3$ | $-(CH_2)_2-C_6H_5$ | 2 | $-C_6H_5$ | $-H$ | $-C_2H_4Si(CH_3)_3$ |
| 12 | $-O-CH_2-C_6H_5$ | $-CH(CH_3)_2$ | 1 | $-C_6H_{11}$ | $-H$ | $-C_2H_4Si(CH_3)_3$ |
| 13 | $-NH-C(O)CH_2-C_6H_5$ | $-CH_2-C_6H_5$ | 2 | $-H$ | $-H$ | $-C_2H_4Si(CH_3)_3$ |
| 14 | $-NH-C_2H_5$ | $-(CH_2)_3-C_6H_5$ | 1 | $-CH_2-C_6H_5$ | $-H$ | $-C_2H_4Si(CH_3)_3$ |
| 15 | $-N(CH_3)_2$ | $-C_2H_5$ | 2 | $-C(CH_3)_3$ | $-H$ | $-C_2H_4Si(CH_3)_3$ |
| 16 | $-NH-CH_2-C_6H_5$ | $-CH_2-C_6H_5$ | 1 | $-H$ | $-H$ | $-C_2H_4Si(CH_3)_3$ |
| 17 | $-OC_2H_5$ | $-(CH_2)_2-C_6H_{11}$ | 2 | $-H$ | $-C_2H_5$ | $-C_2H_4Si(CH_3)_3$ |
| 18 | $-OC_2H_5$ | $-CH_2-O-CH_2-C_6H_5$ | 1 | $-C_6H_5$ | $-H$ | $-C_2H_4Si(CH_3)_3$ |
| 19 | $-OC_2H_5$ | $-(CH_2)_2-S-CH_3$ | 2 | $-C_2H_5$ | $-H$ | $-C_2H_4Si(CH_3)_3$ |
| 20 | $-OC_2H_5$ | $-(CH_2)_3NHC(=NH)NH-NO_2$ | 1 | $-C_6H_5$ | $-H$ | $-C_2H_4Si(CH_3)_3$ |

-continued

| Example | R₃ | R₄ | n | R₅ | R₁ | R₂ |
|---|---|---|---|---|---|---|
| 21 | —OC₂H₅ | —(CH₂)₄NHCOCH₂—C₆H₅ | 1 | —H | —H | —C₂H₄Si(CH₃)₃ |
| 22 | —OH | —CH₂—(1-benzylimidazol-4-yl) | 2 | —H | —H | —C₂H₄Si(CH₃)₃ |
| 23 | —OC₂H₅ | —CH₂—(indol-3-yl) | 1 | —C₆H₅ | —H | —C₂H₄Si(CH₃)₃ |
| 24 | —OC₂H₅ | —CH(CH₂C₆H₅)(NHCOC₆H₅) | 1 | —C₆H₅ | —H | —C₂H₄Si(CH₃)₃ |
| 25 | —OC₂H₅ | —CH(CH₂C₆H₅)(NHCOC₆H₅) | 2 | —H | —H | —C₂H₄Si(CH₃)₃ |
| 26 | —OC₂H₅ | —CH((CH₂)₂C₆H₅)(NHCOC₆H₅) | 1 | —H | —CH₃ | —C₂H₄Si(CH₃)₃ |
| 27 | —OC₂H₅ | —CH(CH₂C₆H₅)(NHCOC₆H₅) | 2 | —C₆H₅ | —H | —C₂H₄Si(CH₃)₃ |
| 28 | —OC₂H₅ | —(CH₂)₂C₆H₅ | 1 | —C₆H₅ | —H | —CH₂—O—C(O)—C(CH₃)₃ |

-continued

| Example | R3 | R4 | n | R5 | R1 | R2 |
|---|---|---|---|---|---|---|
| 29 | —OC$_2$H$_5$ | —(CH$_2$)$_2$—C$_6$H$_5$ | 2 | —C$_6$H$_5$ | —H | $-\underset{\underset{C_6H_{11}}{\|}}{\overset{\overset{H}{\|}}{C}}-O-\overset{O}{\overset{\|}{C}}-C_2H_5$ |
| 30 | —OC$_2$H$_5$ | —(CH$_2$)$_2$—C$_6$H$_5$ | 1 | —C$_6$H$_5$ | —H | $-\underset{\underset{CH(CH_3)_2}{\|}}{CH}-O-\overset{O}{\overset{\|}{C}}-C_2H_5$ |
| 31 | —OC$_2$H$_5$ | —(CH$_2$)$_2$—C$_6$H$_5$ | 1 | —CH$_3$ | —H | $-\underset{\underset{CH(CH_3)_2}{\|}}{CH}-O-\overset{O}{\overset{\|}{C}}-C_6H_5$ |

EXAMPLE 32

(±)-Dihydro-3-[(1-Carboxy-3-phenylpropyl)amino]-4-oxo-1,5-benzothiazepine-5(2H)-acetic acid (a) S-(2-Aminophenyl)-N-[(1,1-dimethylethoxy)carbonyl]-L-cysteine, methyl ester To a mixture of 2-amino-thiophenol (1.9 g., 15.4 mmole), methylene chloride (15 ml.), and 2,6-lutidine (1.8 ml., 1.0 eq.) at −20° (chloroform dry ice) is added 2-[[(1,1 1-dimethylethoxy)carbonyl]amino]-2-propenoic acid, methyl ester (3.0 g., 1.0 eq.) dropwise over 5 minutes. After one hour the cooling bath is removed and the reaction mixture is stirred for an additional 16 hours. The reaction mixture is diluted with ethyl acetate and washed with saturated sodium bicarbonate, water, brine, dried (MgSO$_4$), and evaporated. The residue (4.1 g.) is chromatographed on silica (125 g.) eluting with hexane/ethyl acetate (5:1) to give 2.5 g. of S-(2-aminophenyl)-N-[(1,1-dimethylethoxy)carbonyl]-L-cysteine, methyl ester as an oil after evaporation.

(b) S-(2-Aminophenyl)-N-[(1,1-dimethylethoxy)carbonyl]-L-cysteine

A mixture of S-(2-aminophenyl)-N-[(1,1-dimethylethoxy)carbonyl]-L-cysteine, methyl ester (1.0 g., 3.1 mmole), 1N sodium hydroxide (3.1 ml., 1.0 eq.), and dioxane (6 ml.) is stirred at room temperature in an argon atmosphere for one hour. The reaction mixture is washed with ethyl acetate, neutralized with 1N hydrochloric acid (3.1 ml.) and extracted with methylene chloride (twice). The combined extracts are dried (MgSO$_4$) and evaporated to give 1.0 g. of S-(2-aminophenyl)-N-[(1,1-dimethylethoxy)carbonyl]-L-cysteine as a foam. TLC (methylene chloride/acetic acid/methanol; 100:5:5) major spot at R$_f$=0.5. The product crystallizes from xylene to give S-(2-aminophenyl)-N-[(1,1-dimethylethoxy)carbonyl]-L-cysteine as a fluffy crystalline solid; m.p. 109°–111°.

Anal. calc'd. for C$_{14}$H$_{20}$N$_2$O$_4$S: C, 53.83; H, 6.45; N, 8.97; S, 10.26. Found: C, 53.51; H, 6.28; N, 8.99; S, 10.26.

(c) (±)-(2,3,4,5-Tetrahydro-4-oxo-1,5-benzothiazepin-3-yl)carbamic acid,1,1-dimethylethyl ester A suspension of S-(2-aminophenyl)-N-[(1,1-dimethylethoxy)carbonyl]-L-cysteine (0.65 g., 2.1 mmole) in xylene (15 ml.) is refluxed in a flask equipped with a Dean-Stark trap for 7 hours. Upon cooling of the reaction mixture the product crystallizes. The solid is collected by filtration, washed with xylene, and dried (high vacuum) to give 0.4 g. of (±)-(2,3,4,5-tetrahydro-4-oxo-1,5-benzothiazepin-3-yl)carbamic acid, 1,1-dimethylethyl ester as an off-white crystalline solid; m.p. 197°–200° (decomp.).

Anal. calc'd. for C$_{14}$H$_{18}$N$_2$O$_3$S: C, 57.12; H, 6.16; N, 9.52; S, 10.89. Found: C, 56.88; H, 6.17; N, 9.40; S, 10.87.

(d) (±)-3-[[(1,1-Dimethylethoxy)carbonyl]amino]-3,4-dihydro-4-oxo-1,5-benzothiazepine-5(2H)-acetic acid, ethyl ester A mixture of (±)-(2,3,4,5-tetrahydro-4-oxo-1,5-benzothiazepin-3-yl)carbamic acid, 1,1dimethylethyl ester (0.8 g., 2.7 mmole), tetrahydrofuran (10 ml.) and potassium tert-butoxide (0.4 g., 1.3 eq.) is stirred at 0° (ice bath) under argon for 10 minutes and then treated with ethyl bromoacetate (0.5 g., 1.7 eq.). After 3 minutes the ice bath is removed and the mixture is stirred for one hour. The reaction mixture is then diluted with ethyl acetate and washed successively with saturated sodium bicarbonate, 5% potassium bisulfate, and brine, dried (MgSO$_4$) and evaporated. The residue (1.3 g.) is chromatographed on silica (60 g.) eluting with hexane/ethyl acetate (4:1) to give 1.0 g. of (±)-3-[[(1,1-dimethylethoxy)carbonyl]amino]-3,4-dihydro-4-oxo-1,5-benzothiazepine-5(2H)-acetic acid, ethyl ester as a foam. TLC (hexane/ethyl acetate; 4:1) single spot at R$_f$=0.21.

(e) (±)-3-Amino-3,4-dihydro-4-oxo-1,5-benzothiazepine-5(2H)-acetic acid, ethyl ester A mixture of (±)-3-[[(1,1-dimethylethoxy)carbonyl]amino]-3,4-dihydro-4-oxo-1,5-benzothiazepine-5(2H)-acetic acid, ethyl ester (1.0 g., 2.6 mmole), methylene chloride (5 ml.), and trifluoroacetic acid (3 ml.) is stirred under argon at 25° for 30 minutes. The methylene chloride and trifluoroacetic acid are removed in vacuo and the residue is taken up in ethyl acetate and the hydrochloride salt is precipitated with saturated hydrochloric acid/ethyl ether. The white solid is collected by filtration and washed with 2:1 ethyl acetate/ethyl ether to yield 0.7 g. of (±)-3-amino-3,4-dihydro-4-oxo-1,5-benzothiazepine-5(2H)-acetic acid, ethyl ester as a white solid; m.p. 231°–233° (decomp.). TLC (methylene chloride/acetic acid/methanol; 100:5:5) single spot at $R_f$=0.08.

Anal. calc'd. for $C_{13}H_{16}N_2O_3S \cdot HCl$: C, 49.29; H, 5.41; N, 8.84; S, 10.12; Cl, 11.37. Found: C, 48.87; H, 5.31; N, 8.80; S, 10.05; Cl, 11.37.

(f) (±)-Dihydro-3-[[1-(Ethoxycarbonyl)-3-phenylpropyl]amino]-4-oxo-1,5-benzothiazepine-5(2H)acetic acid, ethyl ester (±)-3-Amino-3,4-dihydro-4-oxo-1,5-benzothiazepine-5(2H)-acetic acid, ethyl ester is reacted with ethyl-2-oxo-4-phenylbutyrate in the presence of sodium cyanoborohydride according to the procedure of Example 1(f) to yield (±)-dihydro-3-[[1-(ethoxycarbonyl)-3-phenylpropyl]amino]-4-oxo-1,5-benzothiazepine-5(2H)-acetic acid, ethyl ester.

(g) (±)-Dihydro-3-[(1-Carboxy-3-phenylpropyl)amino]-4-oxo-1,5-benzothiazepine-5(2H)-acetic acid The diethyl ester product from part (f) is treated with sodium hydroxide according to the procedure of Example 1(h) to yield (±)-dihydro-3-[(1-carboxy-3-phenylpropyl)amino]-4-oxo-1,5-benzothiazepine-5(2H)-acetic acid.

In a similar manner, the keto compounds shown in Col. I of Examples 5 to 31 can be employed in the above procedure to yield other compounds within the scope of the invention.

EXAMPLE 33

(5R)-5-[(1-Carboxy-3-phenylpropyl)amino]dihydro-4-oxo-2-phenyl-2H-1,3-thiazine-3(4H)-acetic acid (B-slow isomer), disodium salt The diacid product from Example 1 (1 mmole) is dissolved in water (50 ml.). Aqueous sodium bicarbonate (0.1 N, 20 ml.) is added and the aqueous solution is lyophilized. The residue is dissolved and purified chromatographically to give (5R)-5-[(1-carboxy-3-phenylpropyl)amino]-dihydro-4-oxo-2-phenyl-2H-1,3-thiazine-3(4H)-acetic acid (B-slow isomer), disodium salt.

In a similar manner disodium or monosodium salts of the products of Examples 2 to 32 can be prepared.

EXAMPLE 34

1000 tablets each containing the following ingredients:

| | |
|---|---|
| (5R)-5[(1-Carboxy-3-phenylpropyl)amino]dihydro-4-oxo-2-phenyl-2H—1,3-thiazine-3(4H)—acetic acid (B slow isomer), disodium salt | 100 mg. |
| Corn starch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the (5R)-5-[(1-carboxy-3-phenylpropyl) amino]dihydro-4-oxo-2-phenyl-2H-1,3-thiazine-3(4H)-acetic acid (B slow isomer), disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar amnner, tablets containing 100 mg. of the product of any of Examples 2 to 32 can be prepared as can tablets containing 50 mg. of active ingredient.

EXAMPLE 35

Two piece #1 gelatin capsules each containing 100 mg. of (±)-dihydro-3-[(1-carboxy-3-phenylpropyl)amino]-4-oxo-1,5-benzothiazepine-5-(2H)-acetic acid, disodium salt are filled with a mixture of the following ingredients:

| | |
|---|---|
| (±)-Dihydro-3-[(1-carboxy-3-phenylpropyl)amino]-4-oxo-1,5-benzothiazepine-5(2H)—acetic acid, disodium salt | 100 mg. |
| Magnesium stearate | 7 mg. |
| Lactose | 193 mg. |
| | 300 mg. |

In a similar manner, capsules containing 100 mg. of the product of any of Examples 1 to 31 and 33 can be prepared.

EXAMPLE 36

An injectable solution is prepared as follows:

| | |
|---|---|
| (5R)-5-[(1-Carboxy-3-phenylpropyl)amino]dihydro-4-oxo-2-phenyl-2H—1,3-thiazine-3(4H)—acetic acid (A-slow isomer), disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1, 2 and 4 to 32.

EXAMPLE 37

1000 tablets each containing the following ingredients:

| | |
|---|---|
| (5R)-5-[(1-Carboxy-3-phenylpropyl)amino]dihydro-4-oxo-2-phenyl-2H—1,3-thiazine-3(4H)—acetic acid (B slow isomer)disodium salt | 100 mg. |
| Avicel | 100 mg. |
| Hydrochlorothiazide | 12.5 mg. |
| Lactose | 113 mg. |

-continued

| Corn starch | 17.5 mg. |
|---|---|
| Stearic acid | 7 mg. |
| | 350 mg. | are prepared from sufficient bulk quantities by slugging the (5R)-5-[(1-carboxy-3-phenylpropyl) amino]dihydro-4-oxo-2-phenyl-2H-1,3-thiazine-3(4H)-acetic acid(B slow isomer) disodium salt, Avicel and a poriton of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 32.

What is claimed is:

1. A compound of the formula:

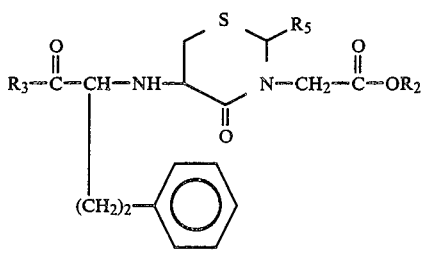

and a pharmacuetically acceptable salt salt thereof wherein:

$R_3$ is hydroxy, ethyoxy, or -O-alkali metal salt ion;
$R_5$ is hydrogen or phenyl;
$R_2$ is hydrogen, alkali metal salt ion, or

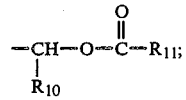

$R_{10}$ is hydrogen, straight or branched chain lower alkyl of 1 to 4 carbons, or cyclohexyl; and
$R_{11}$ is straignt or branched chain lower alkyl of 1 to 4 carbons.

2. The compound of claim 1 wherein:
$R_3$ is ehtoxy: and
$R_2$ is hydrogen.

3. The compound of claim 1 wherein:
$R_3$ is hydroxy; and
$R_2$ is hydrgen.

4. A compound of claim 1 wherein $R_5$ is phenyl.

5. A composition useful for treating hypertension comprising a pharmaceutically acceptable carrier and an effective amount of a hypotensive agent or pharmaceutically acceptable salt thereof of the formula

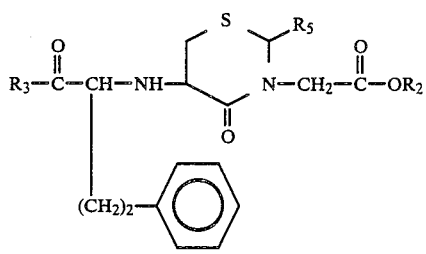

wherein $R_2$, $R_3$, and $R_5$ are as defined in claim 1.

6. A method of treating hypertension in a mammalian species which comprises administering a hypotensively effective amount of the composition of claim 5.

* * * * *